United States Patent
Johnson et al.

(10) Patent No.: US 9,061,953 B2
(45) Date of Patent: Jun. 23, 2015

(54) PROCESS FOR CONVERTING POLYCYCLIC AROMATIC COMPOUNDS TO MONOCYCLIC AROMATIC COMPOUNDS

(71) Applicant: UOP LLC, Des Plaines, IL (US)

(72) Inventors: James A. Johnson, Burr Ridge, IL (US); John Q. Chen, Glenview, IL (US); Peter K. Coughlin, Mundelein, IL (US); Stanley J. Frey, Palatine, IL (US); Vasant P. Thakkar, Elk Grove Village, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 14/471,621

(22) Filed: Aug. 28, 2014

(65) Prior Publication Data
US 2015/0139895 A1    May 21, 2015

Related U.S. Application Data

(60) Provisional application No. 61/906,077, filed on Nov. 19, 2013.

(51) Int. Cl.
| | |
|---|---|
| C07C 4/26 | (2006.01) |
| C07C 4/02 | (2006.01) |
| C07C 5/02 | (2006.01) |
| C10G 47/00 | (2006.01) |
| C07C 4/06 | (2006.01) |
| C07C 4/04 | (2006.01) |
| C10G 1/04 | (2006.01) |
| C07C 7/12 | (2006.01) |
| C01B 3/34 | (2006.01) |

(52) U.S. Cl.
CPC ... *C07C 4/06* (2013.01); *C07C 4/04* (2013.01); *C10G 1/045* (2013.01); *C07C 7/12* (2013.01); *C01B 3/34* (2013.01)

(58) Field of Classification Search
USPC ............ 585/319, 320, 324, 476, 266; 208/67, 208/68, 106, 107
See application file for complete search history.

(56) References Cited

U.S. PATENT DOCUMENTS

| | | | |
|---|---|---|---|
| 3,488,278 A | 1/1970 | Nelson | |
| 3,488,279 A | 1/1970 | Schulman | |

(Continued)

FOREIGN PATENT DOCUMENTS

EP        0082586        6/1983

OTHER PUBLICATIONS

Kamiya et al., "The effect of solvent on the liquefaction of coal as a function of coal rank," Bulletin of the Chemical Society of Japan (1982), 55(12), 3873-3877.

(Continued)

*Primary Examiner* — Thuan D Dang

(57) ABSTRACT

A process for converting polycyclic aromatic compounds to monocyclic aromatic compounds includes pyrolyzing a coal feed to produce a coke stream and a coal tar stream. The coal tar stream is cracked, and the cracked coal tar stream is fractionated to produce an aromatic fraction comprising the polycyclic aromatic compounds. The process further includes hydrocracking the aromatic fraction to partially hydrogenate at least a first portion of the aromatic fraction, and to open at least one ring of a second portion of the aromatic fraction to form the monocyclic aromatic compounds from the polycyclic compounds, and recycling the first portion of the aromatic fraction.

18 Claims, 1 Drawing Sheet

(56) References Cited

U.S. PATENT DOCUMENTS

| | | | |
|---|---|---|---|
| 3,594,303 | A | 7/1971 | Kirk, Jr. et al. |
| 3,594,304 | A | 7/1971 | Seitzer et al. |
| 3,642,607 | A | 2/1972 | Seitzer |
| 3,920,536 | A | 11/1975 | Seitzer et al. |
| 4,022,680 | A | 5/1977 | Maa |
| 4,045,328 | A | 8/1977 | Green et al. |
| 4,048,054 | A | 9/1977 | Green et al. |
| 4,051,012 | A | 9/1977 | Plumlee et al. |
| 4,075,079 | A | 2/1978 | Lang |
| 4,085,033 | A | 4/1978 | Plumlee |
| 4,123,347 | A | 10/1978 | Maa |
| T989,001 | I4 | 12/1979 | Gorin |
| T989,002 | I4 | 12/1979 | Gorin |
| T989,003 | I4 | 12/1979 | Gorin |
| 4,179,352 | A | 12/1979 | Effron |
| 4,189,371 | A | 2/1980 | Maa et al. |
| 4,210,518 | A | 7/1980 | Wilson, Jr. et al. |
| 4,227,989 | A | 10/1980 | Gorbaty et al. |
| 4,259,168 | A | 3/1981 | Liotta |
| 4,283,267 | A | 8/1981 | Maa et al. |
| 4,298,451 | A | 11/1981 | Neuworth |
| 4,311,578 | A | 1/1982 | Fant et al. |
| 4,331,531 | A | 5/1982 | Kuehler |
| 4,334,977 | A | 6/1982 | Derbyshire et al. |
| 4,338,182 | A | 7/1982 | Vernon et al. |
| 4,347,116 | A | 8/1982 | Whitehurst et al. |
| 4,347,117 | A | 8/1982 | Bauman et al. |
| 4,356,077 | A * | 10/1982 | Che ............... 208/412 |
| 4,357,228 | A | 11/1982 | Che |
| 4,374,725 | A | 2/1983 | Whitehurst et al. |
| 4,385,981 | A | 5/1983 | Neskora et al. |
| 4,394,132 | A | 7/1983 | Taylor |
| 4,428,818 | A | 1/1984 | Derbyshire et al. |
| 4,450,066 | A | 5/1984 | Stone et al. |
| 4,452,688 | A | 6/1984 | Mitchell et al. |
| 4,476,009 | A | 10/1984 | Kuhlmann et al. |
| 4,486,293 | A | 12/1984 | Garg |
| 4,537,675 | A | 8/1985 | Silver et al. |
| 4,541,916 | A | 9/1985 | Beuther et al. |
| 4,594,140 | A | 6/1986 | Cheng |
| 4,617,105 | A | 10/1986 | Miller |
| 4,617,106 | A | 10/1986 | Garg |
| 4,626,342 | A | 12/1986 | Garg et al. |
| 4,663,028 | A | 5/1987 | Ditman |
| 4,946,583 | A | 8/1990 | Wurfel |
| 5,110,451 | A | 5/1992 | Jones |
| 5,256,278 | A | 10/1993 | Rindt et al. |
| 5,478,548 | A | 12/1995 | Rogers et al. |
| 7,763,167 | B2 | 7/2010 | Zhang et al. |
| 2013/0267744 | A1 | 10/2013 | Hong et al. |

OTHER PUBLICATIONS

Tempesti et al., "New hydrogen donor solvent for direct liquefaction of coal," La Rivista dei Combustibili (1990), 44(3), 69-72.

Sharma et al.,"Multisolvent successive extractive refining of coal," Energy Sources (1996), 18(1), 1-19.

Koelling et al., "Solvent extraction of coal," Erdoel and Kohle—Erdgas—Petrochemie . . . (1982), 35(2), 50-51.

Bockrath et al., "Evaluation of the donor ability of coal liquefaction solvents," 181st National ACS Meeting—Division of Fuel Chemistry(1981), 26(1), 94-102.

De Marco et al.,"Suitability of coal derived solvents for coal liquefaction processes," 25th Intersociety Energy Conversion Engineering Conference (1990), vol. 5, 448-453.

Anderson et al., "Activated extraction of coal using a hydrogen-donor solvent," Fuel (1974), 53(1), 32-37.

Bate et al., "Coal liquefaction with model solvents containing hydrophenanthrenes . . . ," 201st ACS National Meeting—Division of Fuel Chemistry (1991), 36(2), 490-497.

Burke, F. P., "The role of recycle oil in direct coal liquefaction process development," 209th ACS National Meeting—Division of Fuel Chemistry (1995), 40(2), 216-220.

Chua et al., "Hydroliquefaction of Victorian brown coal in a continuous reactor," Fuel (1987), 66(12), 1680-1684.

Boduszynski et al., "Compositions of distillate recycle solvents derived from direct coal liquefaction in the SRC-I process," Fuel (1985), 64(2), 242-254.

Epperly et al., "Progress in development of exxon donor solvent: Coal liquefaction process," 72nd AIChE Annual Meeting (1979), 26 pages.

Ohe et al., "Reaction mechanism of coal hydrogenation," Fuel (1985), 64(7), 902-905.

Huang et al., "Effect of solvent characteristics on coal liquefaction," 212th ACS National Meeting—Division of Fuel Chemistry (1996), 41(3), 961-966.

Kwon, K.C., "A comparison of anthracene and phenanthrene in coal liquefaction," 88th ACS National Meeting—Division of Fuel Chemistry (1984), 29(5), 139-146.

Futamura, Shigeru, "Roles of hydrogen donor solvents and catalysts in hydrogen transfer . . . ," 208th ACS National Meeting—Division of Petroleum (1994), 39(3), 327-329.

Hetland et al., "Solvent recyclability and hydrotreatment severity in direct liquefaction . . . ," 212th ACS National Meeting—Division of Fuel Chemistry (1996), 41(3), 972-976.

Rusin et al., "Influence of recycle solvent properties on coal extraction," Fuel (1988), 67(8), 1143-1149.

Furlong et al., "Coal processing: The Exxon donor solvent process," Chemical Engineering Progress (1976), 72(8), 69-75.

Kershaw et al., "Supercritical gas extraction of coal with hydrogen-donor solvents," Fuel (1984), 63(8), 1174-1177.

Wade et al., "Exxon donor solvent coal liquefaction process: Development program status VII," AIChE Winter Meeting (1982), 9th, 34 pages.

Rosal et al., "Hydrogen-transferring liquefaction of two different rank coals . . . ," Industrial & Engineering Chemistry Research (1992), 31(10), 2407-2412.

Woodfine et al., "Donor solvent interactions during coal liquefaction," Fuel (1989), 68(3), 293-297.

Stephens, H. P. , "Two-stage coal liquefaction without gas-phase hydrogen," 192nd ACS National Meeting—Division of Fuel Chemistry (1986), 31(4), 314-320.

Kouzu et al., "Conceptual study of hydrogen donor solvent in the NEDOL coal liquefaction process," Journal of Chemical Engineering of Japan (2002), 35(5), 125-136.

Longanbach, James R., "Chemistry of heavy coal liquefaction recycle solvent components," AIChE Spring National Meeting (1984), 24th, 17 pages.

Kang et al., "Donor solvent reactions with coal in a batch-recycle system," 173rd ACS National Meeting—Division of Fuel Chemistry (1977), 22(2), 160-168.

Miller et al., "Upgrading of recycle solvent used in the direct liquefaction . . . ," Industrial & Engineering Chemistry Process Design & Development (1982), 21(1), 170-173.

King et al., "Aspects of the chemistry of donor solvent coal dissolution . . . ," Fuel (1982), 61(3), 257-264.

Search Report dated Feb. 2, 2015 for corresponding PCT Application No. PCT/US2014/065395.

* cited by examiner

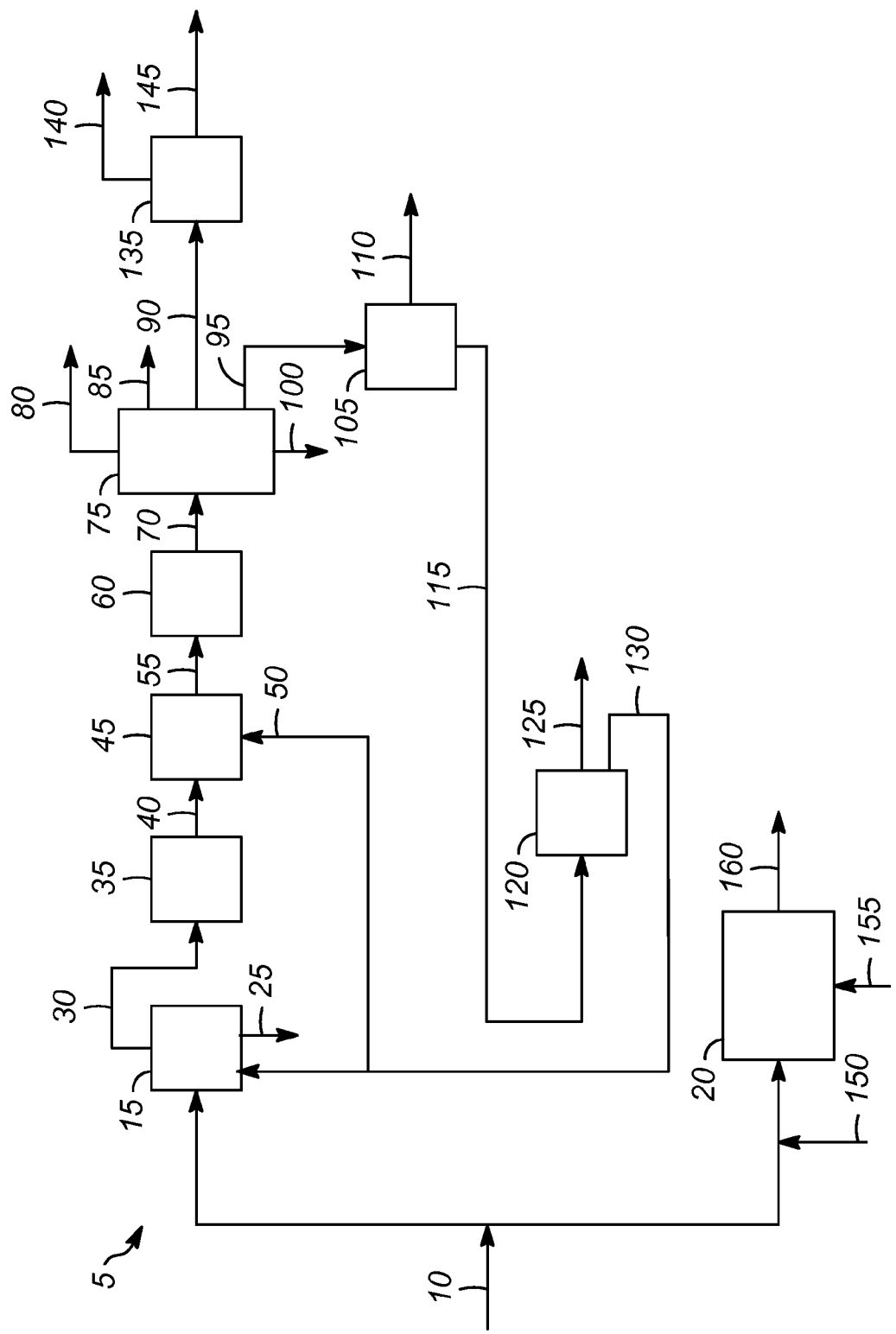

PROCESS FOR CONVERTING POLYCYCLIC AROMATIC COMPOUNDS TO MONOCYCLIC AROMATIC COMPOUNDS

RELATED APPLICATIONS

This application claims priority to U.S. Provisional Application No. 61/906,077 filed on Nov. 19, 2013, the entirety of which is incorporated herein by reference.

BACKGROUND OF THE INVENTION

Many different types of chemicals are produced from the processing of petroleum. However, petroleum is becoming more expensive because of increased demand in recent decades.

Therefore, attempts have been made to provide alternative sources for the starting materials for manufacturing chemicals. Attention is now being focused on producing liquid hydrocarbons from solid carbonaceous materials, such as coal, which is available in large quantities in countries such as the United States and China.

Pyrolysis of coal produces coke and coal tar. The coke-making or "coking" process consists of heating the material in closed vessels in the absence of oxygen to very high temperatures. Coke is a porous but hard residue that is mostly carbon and inorganic ash, which can be used in making steel.

Coal tar is the volatile material that is driven off during heating, and it comprises a mixture of a number of hydrocarbon compounds. It can be separated to yield a variety of organic compounds, such as benzene, toluene, xylene, naphthalene, anthracene, and phenanthrene. These organic compounds can be used to make numerous products, for example, dyes, drugs, explosives, flavorings, perfumes, preservatives, synthetic resins, and paints and stains. The residual pitch left from the separation is used for paving, roofing, waterproofing, and insulation.

Coal tar includes a wide variety or aromatic compounds, including both polycyclic and monocyclic aromatic compounds. However, monocyclic aromatic compounds have broader applicability, and thus more value as end products when compared to polycyclic aromatic compounds.

Thus, there is a need for a process for converting polycyclic aromatic compounds to monocyclic aromatic compounds.

SUMMARY OF THE INVENTION

In a first aspect, a process for converting polycyclic aromatic compounds to monocyclic aromatic compounds includes pyrolyzing a coal feed to produce a coke stream and a coal tar stream. The coal tar stream is cracked, and the cracked coal tar stream is fractionated to produce an aromatic fraction comprising the polycyclic aromatic compounds. The process further includes hydrocracking the aromatic fraction to partially hydrogenate at least a first portion of the aromatic fraction, and to open at least one ring of a second portion of the aromatic fraction to form the monocyclic aromatic compounds from the polycyclic compounds, and recycling the first portion of the aromatic fraction.

In another aspect, a process for converting polycyclic aromatics to monocyclic aromatics includes pyrolyzing a coal feed to produce a coke stream and a coal tar stream. The process further includes cracking the coal tar stream and fractionating the cracked coal tar stream to produce an aromatic fraction comprising naphthalene and alkylnaphthalenes. The aromatic fraction is hydrocracked to partially hydrogenate at least a first portion of the aromatic fraction, and to open one ring of a second portion of the aromatic fraction, and the first portion of the aromatic fraction is recycled.

BRIEF DESCRIPTION OF THE DRAWING

The FIGURE is an illustration of one embodiment of the process of the present invention for converting polycyclic aromatics to monocyclic aromatics.

DETAILED DESCRIPTION OF THE INVENTION

The FIGURE shows one embodiment of a coal conversion process 5 of the present invention. A coal feed 10 can be sent to a pyrolysis zone 15, such as a coking oven, or a gasification zone 20. Alternatively, the coal feed 10 can be split into two parts and sent to both the pyrolysis zone 15 and the gasification zone 20.

In the pyrolysis zone 15, the coal is heated at high temperature, e.g., up to about 2,000° C. (3,600° F.), in the absence of oxygen to drive off the volatile components. Coking produces coke 25 and coal tar stream 30. The coke 25 can be used in other processes, such as the manufacture of steel.

The coal tar stream 30 which comprises the volatile components from the coking process can be sent to an optional contamination removal zone 35, if desired.

The contaminant removal zone 35 for removing one or more contaminants from the coal tar stream 30 or another process stream may be located at various positions along the process depending on the impact of the particular contaminant on the product or process and the reason for the contaminant's removal, as described further below. For example, the contaminant removal zone 35 can be positioned upstream of a separation zone 75. Some contaminants have been identified to interfere with a downstream processing step or hydrocarbon conversion process, in which case the contaminant removal zone 35 may be positioned upstream of the separation zone 75 or between the separation zone 75 and the particular downstream processing step at issue. Still other contaminants have been identified that should be removed to meet particular product specifications. Where it is desired to remove multiple contaminants from the hydrocarbon or process stream, various contaminant removal zones 35 may be positioned at different locations along the process. In still other approaches, a contaminant removal zone 35 may overlap or be integrated with another process within the system, in which case the contaminant may be removed during another portion of the process, including, but not limited to the separation zone 75 or the downstream hydrocarbon conversion zone. This may be accomplished with or without modification to these particular zones, reactors or processes. While the contaminant removal zone 35 is often positioned downstream of the hydrocarbon conversion reactor, it should be understood that the contaminant removal zone 35 in accordance herewith may be positioned upstream of the separation zone 75, between the separation zone 75 and the hydrocarbon conversion zone, or downstream of the hydrocarbon conversion zone or along other streams within the process stream, such as, for example, a carrier fluid stream, a fuel stream, an oxygen source stream, or any streams used in the systems and the processes described herein. The contaminant concentration is controlled by removing at least a portion of the contaminant from the coal tar stream 35. As used herein, the term removing may refer to actual removal, for example by adsorption, absorption, or membrane separation, or it may refer to conversion of the contaminant to a more tolerable compound, or both.

The decontaminated coal tar feed 40 is sent to an optional hydrotreating zone 45. Hydrotreating is a process in which hydrogen donor molecules 50 are contacted with a hydrocarbon stream in the presence of suitable catalysts which are primarily active for the removal of heteroatoms, such as sulfur, nitrogen, and oxygen, and metals from the hydrocarbon feedstock. In hydrotreating, hydrocarbons with double and triple bonds may be saturated. The hydrogen donor molecules 50 can include, for example, hydrogen gas, water, ammonia, hydrogenated aromatic compounds, or any combination thereof. Aromatics may also be saturated. Typical hydrotreating reaction conditions include a temperature of about 290° C. (550° F.) to about 455° C. (850° F.), a pressure of about 3.4 MPa (500 psig) to about 6.2 MPa (900 psig), a liquid hourly space velocity of about 0.5 $hr^{-1}$ to about 4 $hr^{-1}$, and a hydrogen rate of about 168 to about 1,011 $Nm^3/m^3$ oil (1,000-6,000 scf/bbl). Typical hydrotreating catalysts include at least one Group VIII metal, preferably iron, cobalt and nickel, and at least one Group VI metal, preferably molybdenum and tungsten, on a high surface area support material, preferably alumina. Other typical hydrotreating catalysts include zeolitic catalysts, as well as noble metal catalysts where the noble metal is selected from palladium and platinum. The hydrotreated coal tar stream 55 from the hydrotreating zone 45 is routed to a cracking zone 60.

In the cracking zone 60, the hydrotreated coal tar stream 55 is contacted with one or more cracking catalysts to crack hydrocarbons and produce lower molecular weight hydrocarbons. The cracking zone 60 may comprise, for example, a hydrocracking zone, a fluid catalytic cracking zone, or a thermal cracking zone as are known in the art.

Hydrocracking is a process in which hydrocarbons crack in the presence of hydrogen to lower molecular weight hydrocarbons. Typical hydrocracking conditions may include a temperature of about 290° C. (550° F.) to about 468° C. (875° F.), a pressure of about 3.5 MPa (500 psig) to about 27.58 MPa (4,000 psig), a liquid hourly space velocity (LHSV) of about 0.5 to less than about 5 $hr^{-1}$, and a hydrogen rate of about 421 to about 2,527 $Nm^3/m^3$ oil (2,500-15,000 scf/bbl). Typical hydrocracking catalysts include amorphous silica-alumina bases or low-level zeolite bases combined with one or more Group VIII or Group VIB metal hydrogenating components, or a crystalline zeolite cracking base upon which is deposited a Group VIII metal hydrogenating component. Additional hydrogenating components may be selected from Group VIB for incorporation with the zeolite base.

Fluid catalytic cracking (FCC) is a catalytic hydrocarbon conversion process accomplished by contacting heavier hydrocarbons in a fluidized reaction zone with a catalytic particulate material. The reaction in catalytic cracking is carried out in the absence of substantial added hydrogen or the consumption of hydrogen. The process typically employs a powdered catalyst having the particles suspended in a rising flow of feed hydrocarbons to form a fluidized bed. In representative processes, cracking takes place in a riser, which is a vertical or upward sloped pipe. Typically, a pre-heated feed is sprayed into the base of the riser via feed nozzles where it contacts hot fluidized catalyst and is vaporized on contact with the catalyst, and the cracking occurs converting the high molecular weight oil into lighter components including liquefied petroleum gas (LPG), gasoline, and a distillate. The catalyst-feed mixture flows upward through the riser for a short period (a few seconds), and then the mixture is separated in cyclones. The hydrocarbons are directed to a fractionator for separation into LPG, gasoline, diesel, kerosene, jet fuel, and other possible fractions. While going through the riser, the cracking catalyst is deactivated because the process is accompanied by formation of coke which deposits on the catalyst particles. Contaminated catalyst is separated from the cracked hydrocarbon vapors and is further treated with steam to remove hydrocarbon remaining in the pores of the catalyst. The catalyst is then directed into a regenerator where the coke is burned off the surface of the catalyst particles, thus restoring the catalyst's activity and providing the necessary heat for the next reaction cycle. The process of cracking is endothermic. The regenerated catalyst is then used in the new cycle. Typical FCC conditions include a temperature of about 400° C. to about 800° C., a pressure of about 0 to about 688 kPag (about 0 to 100 psig), and contact times of about 0.1 seconds to about 1 hour. The conditions are determined based on the hydrocarbon feedstock being cracked, and the cracked products desired. Zeolite-based catalysts are commonly used in FCC reactors, as are composite catalysts which contain zeolites, silica-aluminas, alumina, and other binders.

The hydrocracked stream 70 is routed to a separation zone 75 where it is separated into two or more fractions 80, 85, 90, 85, 100. Coal tar comprises a complex mixture of heterocyclic aromatic compounds and their derivatives with a wide range of boiling points. The number of fractions and the components in the various fractions can be varied as is well known in the art. A typical separation process involves separating the coal tar into four to six streams. For example, there can be a fraction comprising $NH_3$, CO, and light hydrocarbons, a light oil fraction with boiling points between 0° C. and 180° C., a middle oil fraction with boiling points between 180° C. to 230° C., a heavy oil fraction with boiling points between 230 to 270° C., an anthracene oil fraction with boiling points between 270° C. to 350° C., and pitch.

The light oil fraction contains compounds such as benzene, toluene, xylenes, naphtha, coumarone-indene, dicyclopentadiene, pyridine, and picoline. The middle oil fraction contains compounds such as phenols, cresols and cresylic acids, xylenols, naphthalene, high boiling tar acids, and high boiling tar bases. The heavy oil fraction contains benzene absorbing oil and creosotes. The anthracene oil fraction contains anthracene. Pitch is the residue of the coal tar distillation containing primarily aromatic hydrocarbons and heterocyclic compounds.

As illustrated, the hydrocracked coal tar stream 70 is separated into gas fraction 80 containing gases such as $NH_3$ and CO as well as light hydrocarbons, such as ethane, hydrocarbon fractions 85, 90, and 95 having different boiling point ranges, and pitch fraction 100. Suitable separation processes include, but are not limited to fractionation, solvent extraction, or adsorption.

One or more of the fractions 80, 85, 90, 95, 100 can be further processed, as desired. As illustrated, the fraction 95 is sent to an optional aromatic concentration zone 105. Preferably, the fraction 95 includes hydrocarbons that have an initial boiling point in the range of about 170° C. to about 300° C., and includes at least polycyclic aromatic hydrocarbons such as naphthalene and alkylnaphthalenes. Various known concentration processes such as distillation or crystallization of the fraction 95 can be used to produce a concentrated aromatics stream 115 having a relatively high concentration of polycyclic aromatic compounds. For example, the aromatics stream 115 may include around 30% to 40% by volume of polycyclic aromatic compounds. An effluent stream 110 including compounds removed by the concentration may be subject to additional downstream processing as desired.

The aromatics stream 115 is routed to a hydrocracking zone 120 to undergo a hydrocracking process. As discussed above, the hydrocracking process cracks hydrocarbons in the presence of hydrogen to form lower molecular weight hydrocarbons. Typical hydrocracking conditions may include a temperature of about 290° C. (550° F.) to about 468° C. (875° F.), a pressure of about 3.5 MPa (500 psig) to about 20.7 MPa (3,000 psig), a liquid hourly space velocity (LHSV) of about 1.0 to less than about 2.5 hr$^{-1}$, and a hydrogen rate of about 421 to about 2,527 Nm$^3$/m$^3$ oil (2,500-15,000 scf/bbl). One or more hydrocracking catalysts include amorphous silica-alumina bases or low-level zeolite bases combined with one or more Group VIII or Group VIB metal hydrogenating components, or a crystalline zeolite cracking base upon which is deposited a Group VIII metal hydrogenating component. The zeolitic cracking base can have a mesoporous structure, having pore sizes in the range of about 2 nm to about 50 nm. Additional hydrogenating components may be selected from Group VIB for incorporation with the zeolite base. In particular, the metal used in the hydrocracking catalyst includes one or more of nickel, molybdenum, and tungsten.

During the hydrocracking process, a first portion of the polycyclic aromatic compounds present in the aromatics stream 115 are hydrogenated. Hydrogenation involves the addition of hydrogen to hydrogenatable hydrocarbon compounds. Alternatively, hydrogen can be provided in a hydrogen-containing compound with readily available hydrogen, such as tetralin, alcohols, hydrogenated naphthalenes, and others via a transfer hydrogenation process with or without a catalyst. The hydrogenatable hydrocarbon compounds (that is, the naphthalene and alkylnaphthalenes present in aromatics stream 115) are contacted with a hydrogen-rich gaseous phase and a hydrogenation catalyst in order to hydrogenate at least a portion of the hydrogenatable hydrocarbon compounds to form hydrogenated hydrocarbon compounds including tetralin and alkyltetralins, which can be used as hydrogen donor molecules. The hydrogenated hydrocarbons are output as a stream 130. The hydrogenated hydrocarbons stream 130 may be used to supply hydrogen to an upstream process, or to supplement an existing hydrogen supply. For example, the hydrogenated hydrocarbons stream 130 may be provided to one or both of the pyrolysis zone 15 and the hydrotreating zone 45. When provided to the hydrotreating zone 45, the stream 130 serves as the hydrogen donor stream 50. When the hydrogenated hydrocarbons stream 130 is recycled to the pyrolysis zone 15, the hydrogenated hydrocarbons provide hydrogen donor molecules to pyrolysis, thereby producing a hydrogen-enriched coal tar stream. While the FIGURE shows the hydrogenated hydrocarbons stream 130 recycled to both the pyrolysis zone 15 and the hydrotreating zone 45, it will be appreciated by those of skill in the art that the hydrogenated hydrocarbons stream 130 could alternatively be provided to only one of the pyrolysis zone 15 and the hydrotreating zone 45 without departing from the scope of the invention.

Returning to the hydrocracking zone 120, a second portion of the polycyclic aromatic compounds present in the concentrated stream 115 are cracked, causing at least one aromatic ring to "open," or break, thereby forming monocyclic aromatic compounds. The monocyclic aromatic compounds are output from the hydrocracking zone 120 as a monocyclic aromatic stream 125, and may be subject to further downstream processing, as desired. For example, the monocyclic aromatic stream 125 may undergo downstream transalkylation, alkylation, distillation, isomerization, to control the concentrations of benzene and alkylbenzenes present in the monocyclic aromatic stream 125. For example, it may be desirable to increase a concentration of xylenes in the monocyclic aromatic stream 125, or to increase concentration of one or more particular xylene isomers (i.e., para-xylene, meta-xylene, and/or ortho-xylene).

The transalkylation reaction can be effected in contact with a catalytic composite in any conventional or otherwise convenient manner and may comprise a batch or continuous type of operation, with a continuous operation being preferred. The transalkylation catalyst is usefully disposed as a fixed bed in a reaction zone of a vertical tubular reactor, with the alkylaromatic feed stock charged through the bed in an upflow or downflow manner. The transalkylation zone normally operates at conditions including a temperature in the range of about 130° C. to about 540° C. The transalkylation zone is typically operated at moderately elevated pressures broadly ranging from about 100 kPa to about 10 MPa absolute. The transalkylation reaction can be effected over a wide range of space velocities. That is, volume of charge per volume of catalyst per hour; weight hourly space velocity (WHSV) generally is in the range of from about 0.1 to about 30 hr$^{-1}$. The catalyst is typically selected to have relatively high stability at a high activity level.

For petrochemicals, the alkylation reaction can be performed using an aromatic compound such as benzene or toluene. When using benzene and alkylating with a light olefin such as ethylene or propylene, the product is typically ethylbenzene or cumene. These products can be converted to styrene or phenol plus acetone. When toluene is alkylated with propylene, cymene isomers can be produced, which could be converted into cresols. Aromatic alkylation is generally now conducted with solid acid catalysts including zeolites or amorphous silica-aluminas or ionic liquid catalyst in liquid phase, or alternatively a zeolitic catalyst in vapor phase.

For at least alkylation of aromatic compounds, the temperature range is from about 100° C. to about 225° C. at the pressure range of about 200 kPa to about 7100 kPa in liquid phase, or higher temperature in vapor phase.

Returning to the separation zone 75, a stream 90 including aliphatic $C_6$-hydrocarbons is separated during the separation process in the separation zone 75. The aliphatic $C_6$-hydrocarbons stream 90 is routed to a steam cracking zone 135. Steam cracking is a process in which saturated hydrocarbons are broken down into smaller, often unsaturated, hydrocarbons. It is the principal industrial method for producing the olefins, including ethylene and propylene. The aliphatic $C_6$-hydrocarbons stream 90 is contacted with steam and briefly heated in a furnace without the presence of oxygen. Typically, the reaction temperature is very high, at around 850° C., but the reaction is only allowed to take place very briefly. In modern cracking furnaces, the residence time can be reduced to milliseconds to improve yield. After the cracking temperature has been reached, the gas is quickly quenched to stop the reaction in a transfer line heat exchanger or inside a quenching header using quench oil. The steam cracking process results in output of a hydrogen stream 140 as well as an olefins stream 145. The hydrogen stream 140 may be recycled to various upstream processes or provided to downstream processes as a hydrogen donor. The olefin stream 145 may be collected as an end product of the process or subject to further downstream processing as desired.

In some processes, all or a portion of the coal feed 10 is mixed with oxygen 150 and steam 155 and reacted under heat and pressure in the gasification zone 20 to form syngas 160, which is a mixture of carbon monoxide and hydrogen. The syngas 160 can be further processed using the Fischer-Tropsch reaction to produce gasoline or using the water-gas shift reaction to produce more hydrogen.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention. It being understood that various changes may be made in the function and arrangement of elements described in an exemplary embodiment without departing from the scope of the invention as set forth in the appended claims.

What is claimed is:

1. A process for converting polycyclic aromatic compounds to
monocyclic aromatic compounds comprising:
pyrolyzing a coal feed to produce a coke stream and a coal tar stream;
cracking the coal tar stream;
fractionating the cracked coal tar stream to produce an aromatic fraction comprising the polycyclic aromatic compounds;
hydrocracking the aromatic fraction to partially hydrogenate at least a first portion of the aromatic fraction to form a hydrogenated stream containing tetralin and alkyltetralins, and to open at least one ring of a second portion of the aromatic fraction to form the monocyclic aromatic compounds from the polycyclic compounds;
recycling a first portion of the hydrogenated stream containing tetralin and alkyltetralins to the cracking of the coal tar stream.

2. The process of claim 1, further comprising hydrotreating the coal tar stream to remove one or more of nitrogen, sulfur, and oxygen contaminants from the coal tar stream, and wherein said cracking step cracks the hydrotreated coal tar stream.

3. The process of claim 2, wherein a second portion of the hydrogenated stream containing tetralin and alkyltetralins is recycled to the hydrotreating.

4. The process of claim 1, wherein the aromatic fraction comprises aromatic hydrocarbons having an initial boiling point from about 170° C. to about 300° C.

5. The process of claim 1, wherein the polycyclic aromatic compounds comprise naphthalene and alkylnaphthalenes.

6. The process of claim 1, further comprising increasing a concentration of the polycyclic aromatic compounds in the aromatic fraction.

7. The process of claim 6, wherein said step of increasing the concentration comprises distilling the aromatic fraction.

8. The process of claim 7, wherein said step of increasing the concentration increases the concentration of the polycyclic aromatic compounds in the concentrated aromatic fraction to a range of about 30% to about 40%.

9. The process of claim 1, wherein said hydrocracking comprises contacting the aromatic fraction with a zeolitic catalyst including a metal function.

10. The process of claim 9, wherein said metal function includes one or more of nickel, molybdenum, and tungsten.

11. The process of claim 1, wherein said fractionating further produces an aliphatic stream comprising $C_6$-aliphatic hydrocarbons.

12. The process of claim 11, further comprising:
steam cracking the aliphatic stream to produce one or more of ethylene and propylene.

13. The process of claim 12, wherein said step of steam cracking further produces hydrogen.

14. A process for converting polycyclic aromatics to monocyclic aromatics comprising:
pyrolyzing a coal feed to produce a coke stream and a coal tar stream;
cracking the coal tar stream;
fractionating the cracked coal tar stream to produce an aromatic fraction comprising naphthalene and alkylnaphthalenes;
hydrocracking the aromatic fraction to partially hydrogenate at least a first portion of the aromatic fraction to form a hydrogenated stream containing tetralin and alkyltetralins, and to open one ring of a second portion of the aromatic fraction; and
recycling a first portion of the hydrogenated stream containing tetralin and alkyltetralins to the cracking of the coal tar stream.

15. The process of claim 14, wherein said hydrocracking comprises contacting the aromatic fraction with a zeolitic catalyst including a metal function.

16. The process of claim 15, wherein said zeolitic catalyst has a mesoporous structure.

17. The process of claim 14, further comprising hydrotreating the coal tar stream to remove one or more of nitrogen, sulfur, and oxygen contaminants from the coal tar stream, and wherein said cracking step cracks the hydrotreated coal tar stream.

18. The process of claim 17, wherein a second portion of the hydrogenated stream containing tetralin and alkyltetralins is recycled to the hydrotreating.

\* \* \* \* \*